United States Patent [19]

Masilamani et al.

[11] Patent Number: 5,171,880
[45] Date of Patent: Dec. 15, 1992

[54] OXIDATION OF ORGANIC COMPOUNDS HAVING BENZYLIC CARBON ATOMS IN WATER

[75] Inventors: Divakaran Masilamani, Morristown; David M. Hindenlang, Randolph, both of N.J.

[73] Assignee: Allied-Signal Inc., Morristown, N.J.

[21] Appl. No.: 669,719

[22] Filed: Mar. 15, 1991

Related U.S. Application Data

[63] Continuation-in-part of Ser. No. 91,625, Sep. 1, 1987.

[51] Int. Cl.$^5$ .............................................. C07C 51/16
[52] U.S. Cl. ................................. 562/411; 568/309; 568/426; 568/910
[58] Field of Search ............... 562/411; 568/309, 426, 568/910

[56] References Cited

U.S. PATENT DOCUMENTS 2,900,412  8/1959  Toland, Jr. ........................ 562/411
2,903,480  9/1959  Toland, Jr. ........................ 562/411

*Primary Examiner*—Arthur C. Prescott
*Attorney, Agent, or Firm*—R. C. Stewart, II; G. H. Fuchs; D. L. Webster

[57] ABSTRACT

The present invention is directed to a process of oxidizing organic compounds having benzylic carbon atoms. The process of this invention comprises reacting an organic compound having one or more benzylic carbon atoms with an effective amount of an effective oxidizing agent in water at a temperature equal to or greater than about 350° C. and at a pressure equal to or greater than about 175 atmospheres, wherein said agent is selected from the group consisting of a combination of one or more bases and one or more of elemental sulfur, an oxidized form of elemental sulfur and/or an organic or inorganic sulfur containing compounds capable of forming elemental sulfur, said oxidized forms or a combination thereof in situ under process conditions, and organic or inorganic compounds which form one or more bases and elemental sulfur, oxidized forms of sulfur or a combination thereof in situ under process conditions.

30 Claims, No Drawings

OXIDATION OF ORGANIC COMPOUNDS HAVING BENZYLIC CARBON ATOMS IN WATER

RELATED APPLICATIONS

This application is a continuation in part application of U.S. patent application Ser. No. 091,625 filed Sep.1, 1987.

BACKGROUND OF THE INVENTION

1. Field of the Invention

This invention relates to the oxidation of organic compounds having benzylic carbon atoms. More particularly, this invention relates to such oxidation which is carried out by reacting such compounds with an effective amount of a sulfur containing compound in water at high temperatures and pressures in the presence of a base.

2. Prior Art

The oxidation of organic compounds having benzylic carbons with sulfur or sulfur dioxide in the presence of water is known. For example, U.S. Pat. No. 2,900,412 discloses that lower alkyl aromatic hydrocarbons, lower alkyl benzoic acids, and partial oxidation products of such hydrocarbons and acids, for example, alcohols, aldehydes, ketones, and the like, may be oxidized to produce aromatic carboxylic acids by heating these materials in the absence of an inorganic base with water and sulfur dioxide to a temperature in the range from 550° to 800° F. under a superatmospheric pressure, preferably sufficient to maintain a part of the water in liquid phase.

U.S. Pat. No. 2,903,480 describes a process for oxidizing organic compounds in which the effective oxidizing agent is sulfur in which an organic compound, elemental sulfur and water are intimately contacted with each other at a temperature above about 500° F. The reactants may be in liquid phase, vapor phase or mixed liquid and vapor phase during the contact.

SUMMARY OF THE INVENTION

The present invention is directed to a process for oxidizing organic compounds having one or more benzylic carbon atoms. More particularly, the process of this invention comprises reacting an organic compound having one or more benzylic carbon atoms with an effective amount of an effective oxidizing agent in water at a temperature equal to or greater than about 50° C. and at a pressure equal to or greater than about 175 atmospheres, where said agent is selected from the group consisting of the combination of one or more a bases and one or more sulfur containing compounds selected from the group consisting of elemental sulfur, oxidized forms of elemental sulfur, and combinations thereof. Surprisingly, it has been discovered that though use of the combination of the sulfur containing compounds and base, either by direct addition, by in situ formation or a combination therefore yields of the "fully oxidized" product are higher providing for greater selectivity. As used herein, "fully oxidized" means that where the benzylic carbon is directly substituted to an aliphatic carbon atom or unsubstituted, the benzylic carbon is oxidized to a carboxyl group, and where the benzylic carbon atom, is substituted directly to an aromatic or heteroaromatic carbon atom the benzylic carbon is oxidized to a keto function.

DESCRIPTION OF THE PREFERRED EMBODIMENTS

In the process of this invention, an organic compound having one or more benzylic carbon atoms is reacted with an effective amount of an "effective oxidizing agent" at a temperature equal to or greater than about 350° C., and at a pressure equal to or greater than 175 atmospheres. As used herein, an "organic compound having one or more or benzylic carbon atoms" is an aromatic or heterocyclic compound having a carbon-atom bonded directly to at least one aromatic or heterocyclic moiety.

Illustrative of such compounds are arenes such as alkylbenzene, substituted alkylbenzene and other mono and polysubstituted aromatics including toluene, xylenes, mesitylene, benzylchloride, o-chlorotoluene, p-chlorotoluene, ethylbenzene, benzal chloride, 2-bromo-1-phenylethane, benzylbromide, o-nitrotoluene, n-butylbenzene, benzylmercaptan, 1,2,4,5-tetramethyl benzoic acid, 1-phenylethanol, 1-phenyl-2-chloropropane, 1-phenylpropene, 1-phenylpropanol, 3-phenylpropene, 1-phenylethylene glycol, phenylacetylene, 1-acetamide,2-nitro naphthalene, 1-acethylnaphthalene, 2-acetyl-laminonaphthalene, 1-amino-3-methylnaphthalene, 2-amino-6-methylnaphthalene, 1-(2-aminoethyl)-naphthalene, 2-benzyl-1-hydroxynaphthalene, 1,5-diamino- 2-methylnaphthalene, 1,6-dimethyl-4-isopropyl- naphthalene, 2,3-dimethylnaphthalene, 2-ethylnaphthalene, 1,2,7-trimethylnaphthalene, 10-methyl-1,2-benzanthracene, benzaldehyde, 2-methylbenzaldehyde, 9,10-dimethyl-1,2-benzanthracene, 3,4-dimethylbenzaldehyde, 3,3'-dimethyl-1,1-binaphthyl, 1,3,5-triacethylbenzene, 4,4'-dihdroxy-3,3' diethyl-5,5'-dimethylbiphenyl, benzophenone, 2,4,5-trimethylbenzoic acid, 2-(2-tolyyl)benzoic acid, 4,4'dimethylbenzophenone, 2,3'dimethylbiphenyl, 4,4'-dimethylbiphenyl, 4-methylbenzophenone, 1,3-dimethylanthracene, 9-ethylanthracene, 2,3-dimethylanthracene, 2-methyl-antracene, 9-acetylphenanthrene 7-methylphenanthrene, 9-ethylphenanthrene, and the like.

Also illustrative of useful benzylic compounds are substituted heterocyclic compounds as for example, 5,6-dimethylbenzimidazole, 5-methyl-benzimidazole, 2-methylbenzofuran, 5-methyl-benzofuran, 7-methylbenzofuran, 2-methylbenzothiazole, 5-chloro -2- methylbenzothiazole, 2-methyl-2-iminobenzothiazolene, 2-methylbenzoxazole, and the like.

Preferred for use in the practice of this invention are arenes in which the benzylic carbon is not oxidized as for example a methyl, or ethyl group and those in which the benzylic carbon atom has been oxidized to form a carbon atom substituted with a hydroxy group or a carbonyl (ketone or aldehyde) group. Where the carbon atom adjacent to the benzylic carbon is aliphatic i.e. alkyl, ketone, aldehyde, alkoxy and the like, the benzylic carbon atoms is oxidized to the carboxylic acid function in high yields. This material may be conveniently decarboxylated to form the unsubstituted arene. Where the benzylic carbon atom is substituted to an aromatic or heteroaromatic function, such as benzylphenone, the benzylic carbon atom is oxidized to the corresponding keto functions in good yields.

Particularly preferred for use in the practice of this invention are benzene naphthalene, anthracene or phenathacene substituted with one or more substituents at least one of which is an alkyl group. Other compounds having benzylic carbon atoms which are particularly suited for use in the process of this invention are naturally occurring materials or process residues from such materials which comprise arenes having one or more alkyl substituents such as low grade coals as for example lignite and bituminous coals, heavy crude oil, heavy hydrocarbons extracted from tar sands, commonly called tar sand bitumen, such as Athavasca tar sand bitumen obtained from Canada, heavy petroleum crude oils, such as Venezuelan Orinoco heavy oil belt crudes (Boscan heavy oil), heavy hydrocarbon fractions obtained from crude petroleum oils particularly heavy vacuum gas oils, vacuum residues, petroleum tars, coal tars and shale oils. These naturally occurring materials, which may contain alkyl substituted arenes, can be conveniently processed in accordance with this invention to produce carboxylic acid substituted arenes such as benzoic acid, 1-anthracene carboxylic acid, 1-napthalene carboxylic acid or 1-phenathrene carboxylic acid, which can be decarboxylated to form the corresponding decarboxylated arene such as benzene, anthracene or phenathrene.

The process is carried out in the presence of effective oxidizing agents. Effective oxidizing agents are selected from the group consisting of combination of one or more bases and one or more sulfur containing compounds selected from the group consisting of elemental sulfur, oxidized forms of elemental sulfur. Surprisingly, it has been discovered that the combination of sulfur, sulfur dioxide or a combination thereof and a base increases the effectiveness of the oxidizing agent which increases the formation of the fully oxidized product, and decreases the percent yield of oxidation by-products such as various intermediate oxidation by-products. The combination of a base and elemental sulfur, oxidized forms of sulfur or a combination thereof can be formed by direct addition of the base and the sulfur compound or such a combination can be formed in situ. For example, such a combination can be formed by direct addition of an inorganic or organic base such as an inorganic or organic alkoxide, carbonate, bicarbonate, alkali metal and alkaline earth metal hydroxide or oxide, as for example sodium hydroxide, potassium hydroxide, calcium hydroxide, magnesium hydroxide, sodium methoxide, sodium ethoxide, sodium carbonate, barium hydroxide and the like and elemental sulfur, an oxidized form thereof such as sulfur dioxide, sulfur trioxide. Such a combination can also be formed in situ by addition of one or more bases and one or more compounds which form elemental sulfur oxidized forms of sulfur or a combination thereof under process conditions as for example organo sulfur compounds such as mercaptans, such as ethylmercaptan and methyl mercaptan; dialkylsulfites, dialkylsulfides, and the like. Alternatively, such a combination can be formed in situ by the decomposition of compounds which form combination of a base and said elemental sulfur and/or sulfur dioxide in situ as for example oxyacids such as sulfurous oxyacids of sulfur which generate sulfur dioxide and base on heating in water, such as sulfurous acid, and hydro-sulfurous acid, and metal and non-metal salts thereof such as metal and non-metal sulfites and bisufites as for example ammonium sulfite, ammonium bisulfite, sodium sulfite, sodium bisulfite, calcium sulfite, calcium bisulfite, and the like.

Preferred for use in the practice of this invention as the oxidizing agent is the combination of one or more a inorganic bases and one or more sulfur containing compound selected from the group consisting elemental sulfur, sulfur dioxide, and sulfur containing inorganic acids such as sulfurous acid, hydrosulfrous acid, and their salts, inorganic sulfites and bisulfites, preferably the ammonium, alkali metal and alkaline earth metal sulfites and bisulfites or a combination thereof. Particularly preferred for use in the practice of this invention is the combination of a base preferably an alkali metal or alkaline earth metal hydroxide and elemental sulfur, sulfuric dioxide or a combination thereof or inorganic bisulfite salts, sulfite salts or a combination thereof which form such a combination in situ.

An "oxidizing effective amount" of one or more effective oxidizing agents is employed. As used herein, an "oxidizing effective amount" is an amount of such agents which is effective to oxidized the desired number of benzylic carbon atoms to the fully oxidized Product. In general, the amount of oxidizing agent employed is such that the amount of base and of sulfur in the reaction mixture is at least 0.9 equivalents (each of the base and sulfur containing compounds) based on the total equivalents of oxidizable benzylic carbon atoms contained in the organic compound. The upper limit for the oxidizing agent is not critical. In general, to obtain desired stoichiometric oxidation of benzylic carbon atoms, the amount employed is at least about the stoichiometric amount required to form the desired oxidation product. In the preferred embodiments of the invention, the amount of oxidizing agent employed is from about 1.0 equivalent to about 3.0 equivalents based on the total equivalents of oxidizable benzylic carbon atoms contained in the organic compound to form the desired oxidation product, and in the particularly preferred embodiments, the amount of oxidizing agent employed is from about 1.5 to about 2.5 equivalents on the aforementioned basis. Amongst these particularly preferred embodiments, most preferred are those embodiments in which the amount of oxidizing agent is 200% of the stoichiometric amount required to oxidized the oxidizable benzylic carbon atoms contained in the organic compound to form the desired oxidation product.

The amount of water employed is not critical. In general, an amount is employed which is sufficient to dissolve the organic compound to some degree at the process temperature and pressures. In general, the amount of water is at least about ten times the total number of moles of the organic compound. While the upper amount of the water is not critical, in general, the amount employed is not less than about 5.0 times the total weight of the organic compound. In the preferred embodiments of the invention, the amount of water is from about seven to about nine times the total weight of the organic compound and the oxidizing agent.

Process temperatures and pressures are critical. In general, the process is carried out at a temperature equal to or greater than about 350° C. and a pressure equal to or greater than about 175 atmospheres. In the preferred embodiments of the invention, the process is carried out at a temperature equal to or greater than about 360° C. and a pressure equal to or greater than about 200 atmospheres, and in the particularly preferred embodiments of this invention, the process is carried out at supercritical conditions of water, i.e., temperatures equal to or greater than about 374° C. and pressure equal to or greater than about 218.3 atmospheres. Amongst these particularly preferred embodiments, most preferred are those embodiments in which process temperatures are about 400° C. and at a pressure of about 225 atmospheres.

The process is carried out for a time sufficient to oxidize the benzylic carbon atom to the desired extent. Residence times are not critical and can vary widely depending on such factors as the susceptibility of the benzylic carbon atoms to oxidation, the reaction temperature and pressure and the like. Usually residence times are in the range of from about 0.1 to about 5 hours. In the preferred embodiments of the invention residence times are from about 0.5 to about two hours, and in the particularly preferred embodiments residence times are in the range of from about 0.75 to about 1.25 hours.

The process of this invention can be conducted in batch, semicontinuous of continuous fashion. In the preferred embodiments of the invention, the Process is carried out in a semi-continuous or continuous fashion, and in the particularly preferred embodiments of the invention, the reaction is carried out in a continuous fashion.

The reaction may be conducted in a signle reaction zone or in a plurality of reaction zones, in series or in parallel or it may be conducted intermittently or continuously in an elongated tubular zone or series or such zones. The materials of construction employed should be inert to the reactants during the reaction and the fabrication of the equipment should be able to withstand the reaction temperatures and pressure.

The reaction zone can be fitted with one or more internal and/or external heaters in order to control undue temperature fluctuations, or to prevent any possible "runaway" reaction temperatures. In preferred embodiments of the process, agitation means to vary the degree of mixing the reaction mixture can be employed. Mixing by vibration, shaking, stirring, rotation, oscillation, ultrasonic vibration or the like are all illustrative of the type of agitation means contemplated. Such means are available and well known to those skilled in the art.

The reactants and reagents may be initially introduced into the reaction zone simultanepusly or stepwise or it may be continuously or intermittently introduced in such zone during the course of the process. Means to introduce and/or adjust the quantity of reactants introduced, either intermittently or continuously into the reaction zone during the course of the reaction can be conveniently utilized in the process especially to maintain the desired molar ratio of the reaction solvent, reactants and reagents.

The oxidized products formed by the process of this invention can be recovered using standard recovery techniques and accordingly will not be described in great detail. Illustrative of useful recovery techniques are distillation, absorption, absorption and extraction. Such procedures are described in detail in Perry's Chemical Engineering Handbook published by McGraw-Hill, Inc., which is incorporated herein by reference.

Oxidized products produced by the process of this invention have many uses. For example, materials such as benzaldehyde, toluene, xylene, ethylbenzene, and heavy hydrocarbons such as heavy crude oil, heavy hydrocarbons extracted from tar sands commonly called tar sand bitumen, such as Athabasca tar sand bitumen obtained from Canada, heavy petroleum crude oils, such as Venezuelan Orinoco heavy oil belt crudes (Boscan heavy oil), heavy hydrocarbon fractions obtained from crude petroleum oils particularly heavy vacuum gas oils, vacuum residue as well as petroleum tar and coal tar or even shale oil can be reacted in the process of this invention with a suitable oxidizing agent such as elemental sulfur, or sulfur dioxide to form benzene, a useful industrial solvent, as well as other polynuclear atomatics.

The following examples are present to better illustrate the invention and should not be construed as limitation thereon.

COMPARATIVE EXAMPLES 1 to 10

Reactions were carried out in stainless steel microreactors made of Swagelop capped ends (¼" diameter). Ten mmols of each of bibenzyl, deoxybenzoin and toluene with sulfur or sulfur dioxide (3 molar excess) was weighed and reacted with 1.35g (75mmols) of water. The microreactor was placed in Wood's Alloy bath heated by electric tapes. The temperature was controlled accurately to ±2° using a Datatrak system. The heating was usually carried out for one hours. The microreactor was cooled in cold water and the contents extracted with $CCl_4$ (or other suitable organic solvents). The organic layer was dried and concentrated. The water layer was also concentrated to see if there were any products dissolved in it. Analysis using capillary column electron impact and chemical ionization gc/mass spectrometry, 'HNMR and/or showed that nonadecane did not react and was recovered quantitatively. The results of these experiments are set forth in Table I.

In Table I, the abreviations shall have the following meanings.
a. "T" is Toluene;
b. "BA" is Benzoic Acid;
c. "B" is Benzene;
d. "BB" is Bibenzyl;
e. "DOB" is Deoxybenzoin; and
f. "BT" is Benzothiophene.

TABLE I

| Comp. Ex. No. | Reactant | Reagent | Temperature | Products (Mole %) | | | | | |
|---|---|---|---|---|---|---|---|---|---|
| | | | | T | BA | B | BB | DOB | BT |
| 1 | BB | S° | 400° C. | 44 | 33 | 22 | 1 | 0 | 0 |
| 2 | DOB | S° | 400° C. | 10 | 10 | 20 | 2 | 38 | 17 |
| 3 | T | S° | 400° C. | 55.5 | 30.5 | 14.0 | Trace | 0 | 0 |
| 4 | T | S° | 350° C. | 61.4 | 27.2 | 10.0 | 1.4 | 0 | 0 |
| 5 | T | S° | 300° C. | 77.0 | 23.0 | 0 | 0 | 0 | 0 |
| 6 | T | S° | 250° C. | 100 | 0 | 0 | 0 | 0 | 0 |
| 7 | T | $SO_2$ | 400° C. | 39.4 | 42.4 | 15.1 | 3.0 | 0 | 0 |
| 8 | T | $SO_2$ | 350° C. | 35.3 | 58.4 | 5.0 | 1.2 | Trace | 0 |
| 9 | T | $SO_2$ | 300° C. | 56.3 | 36.7 | 3.0 | 4.0 | Trace | 0 |
| 10 | T | $SO_2$ | 250° C. | 100 | 0 | 0 | 0 | 0 | 0 |

COMPARATIVE EXAMPLE 11

When diphenylmethane or benzophenone were heated with one molar ratio of sulfur in water at 400° C.

for one hour as described Comparative Examples 1 to 10, the same equilibrium mixture of diphenylmethane (35%) and benzophenone (65%) was obtained.

EXAMPLE 1

When diphenylmethane was heated in water (containing one mole ratio of sodium bisulfite) at 400° C. for one hour as described in comparative Examples 1 to 10, it was converted quantitatively to benzophenone.

COMPARATIVE EXAMPLE 12

When heated with one mole equivalent of sulfur in water at 400° C. as described in Comparative Examples 1 to 10, ethylbenzene is converted to acetophenone, toluene, benzoic acid and benzene.

COMPARATIVE EXAMPLE 13

When acetophenone was heated with one mole equivalent of sulfur in water at 400° C. for one hour (as described in Comparative Examples 1 to 10), it was converted to a product mixture almost identical to the one obtained in Comparative Example 16.

COMPARATIVE EXAMPLE 14

Ten millimoles of diphenylmethane was heated at 400° C. for 1 hour with 1.35 ml of water saturated with sulfur dioxide in the microreactor described in Comparative Examples 1 to 10. After cooling, the product was entracted with ether. The ether layer was dried ($Na_2SO_4$) and concentrated to yield 95% of benzophenone and 5% of diphenylamine. Colloidal sulfur was observed in the aqueous layer.

EXAMPLE 2

Ten millimoles of toluene was heated at 400° C. for 1 hour with 1.35 ml of water containing 20 millimoles of sodium bisulfite. In cooling, a white spherical solid coated with pale yellow powder was observed. The solid was filtered, ground and dissolved in $D_2O$. NMR analysis showed that the solid was made entirely of the sodium salt of benzoic acid. The yield was guanhitative. Extraction of the aqueous layer with ether showed no toluene.

EXAMPLE 3

Under conditions identical to those described in Example 2, p-xylene formed the disodium salt of terephthalic acid in 95% yield. Small amounts (<5%) of sodium salt of p-methylbenzoic acid were also formed. However, it was necessary to use 40 millimoles of sodium bisulfite.

EXAMPLE 4

Ten millimoles of ethylbenzene were heated at 400° C. for 1 hour with 1.35 ml of water containing 20 millimoles of sodium bisulfite. On cooling, the sodium salt of benzoic acid was formed as a hard solid (see Example 2) in more than 90% yield.

EXAMPLE 5

Under the same condition as described in Example 4, acetophenone was converted into the sodium salt of benzoic acid in 95% yield.

EXAMPLE 6

Ten millimoles of ethylbenzene were heated at 400° C. for 1 hour with 1.35 ml of water containing 20 millimoles of sodium sulfite and 10 millimoles of lead nitrate. On cooling, a suspension of black precipitate was observed. The reaction product was extracted with ether and the ether layer was dried over $Na_2SO_4$ and concentrated to yield acetophenone in more than 95% yield. Acetophenone was confirmed by NMR and gas chromatographic techniques.

EXAMPLE 7

Under the experimental conditions described under Example 4, p-diethylbenzene was the disodium salt, benzoic acid in 90% yield. However, 40 millimoles of sodium sulfite were used.

What is claimed is:

1. A process for oxidizing benzylic carbon atoms which comprises reacting an organic compound having one or more benzylic carbon atoms with an oxidizing effective amount of an effective oxidizing agent in water at a temperature equal to or greater than about 350° C. and at a pressure equal to or greater than about 175 atmospheres, said effective oxidizing agent selected from the group consisting of combinations of one or more bases and elemental sulfur, the oxidized forms of elemental sulfur or a combination of sulfur and said oxidized forms.

2. A process of claim wherein said process is carried out at a temperature equal to or greater than about 360° C. and a pressure equal to or greater than about 200 atmosphere.

3. A process according to claim wherein said process is carried out at a temperature and pressure equal to or greater than the critical temperature and pressure of water.

4. A process according to claim wherein said temperature is equal to about 400° C.

5. A process according to claim wherein said effective oxidizing agent is selected from the group consisting of the combination of one or more bases and elemental sulfur oxidized forms.thereof, or a combination thereof.

6. A process according to claim wherein said effective oxidizing agent is sulfur and one or more bases.

7. A process according to claim wherein said effective oxidizing agent is selected from the group consisting of any combination of one or more bases and sulfur dioxide, sulfur containing oxy acids which form sulfur dioxide under process conditions, and the salts of said acids.

8. A process according to claim wherein said effective oxidizing agent is inorganic sulfites, inorganic bisulfites or sulfites and a combination thereof.

9. A process according to claim wherein said agent is a combination of one or more inorganic bases and sulfur dioxide.

10. A process according to claim wherein said agent is selected from the group consisting of a combination of one or more inorganic bases and sulfur containing oxy acids which form sulfur dioxide under process conditions and the salts thereof.

11. A process according to claim wherein said acids are selected from the group consisting of sulfurous acid, hydrosulfurous acid, and the salts thereof.

12. A process according to claim wherein said agent is selected from the group consisting of the alkaline earth metal, alkali metal and ammonium salts of said acids.

13. A process according to claim wherein said agent is selected from the group consisting of inorganic bisulfite salts, sulfite salts or a combination thereof.

14. A process according to claim wherein said organic compounds are selected from the group consisting of substituted arenes wherein at least one of the substituents is an alkyl group.

15. A process according to claim wherein said arenes are selected from the group consisting of alkyl substituted benzene, anthracene, phenanthrene, and naphthalene.

16. A process according to claim wherein said arenes are selected from the group consisting of alkyl substituted benzene.

17. A process according to claim wherein said organic compounds comprise heavy hydrocarbons.

18. A process according to claim wherein said heavy hydrocarbons are sleected from the group consisting of low grade coals, heavy crude oil, heavy hydrocarbons extracted from tar sands, heavy petroleum crude oils, shale, oils, and heavy hydrocarbon fractions obtained from crude petroleum oils.

19. A process according to claim wherein the amount of said oxidizing agent is at least about 0.9 equivalents based on the total equivalents benzylic carbon atoms.

20. A process according to claim wherein said amount is from about 1.0 to about 5.0 equivalent %.

21. A process according to claim wherein said amount is from about 2.0 to about 4.0 equivalent %.

22. A process according to claim wherein an excess of said oxidizing agent is used.

23. A process according to claim 13 wherein said effective oxidizing agent is an alkali metal bisulfite.

24. A process according to claim 23 wherein said alkali metal bisulfite is sodium bisulfite.

25. A process according to claim 1 wherein said organic compound is an arylmethylenearyl compound.

26. A process according to claim 25 wherein said arylmethylenearyl compound is diphenylmethane.

27. A process according to claim 25 wherein said agent is an alkali metal bisulfite 28. A process according to claim 27 wherein said agent is sodium bisulfite.

29. A process according to claim 26 wherein said agent is an alkali metal bisulfite.

30. A process according to claim 29 wherein said alkali metal bisulfite is sodium bisulfite.

* * * * *